(12) United States Patent
Richard et al.

(10) Patent No.: US 8,980,793 B2
(45) Date of Patent: Mar. 17, 2015

(54) PHYTOSANITARY FORMULATIONS

(75) Inventors: Claire Richard, Beaumont (FR); Alexandra Ter Halle, Lezoux (FR); Gérard Ledoigt, Romagnat (FR)

(73) Assignees: Centre National de la Recherche Scientifique (CNRS), Paris (FR); Universite Blaise Pascal-Clermont-Ferrand II, Clermont-Ferrand Cedex (FR)

( * ) Notice: Subject to any disclaimer, the term of this patent is extended or adjusted under 35 U.S.C. 154(b) by 741 days.

(21) Appl. No.: 12/523,229

(22) PCT Filed: Jan. 25, 2008

(86) PCT No.: PCT/IB2008/001007
§ 371 (c)(1),
(2), (4) Date: Aug. 6, 2009

(87) PCT Pub. No.: WO2008/090476
PCT Pub. Date: Jul. 31, 2008

(65) Prior Publication Data
US 2010/0016161 A1   Jan. 21, 2010

Related U.S. Application Data

(60) Provisional application No. 60/886,544, filed on Jan. 25, 2007.

(51) Int. Cl.
*A01N 25/00* (2006.01)
*A01N 63/00* (2006.01)
*A01N 35/00* (2006.01)
*A01N 59/02* (2006.01)
*A61K 33/04* (2006.01)
*A61K 36/00* (2006.01)
*A01N 65/00* (2009.01)
*A61K 36/87* (2006.01)

(52) U.S. Cl.
CPC ...................................... *A01N 65/00* (2013.01)
USPC ........ 504/116.1; 504/118; 504/348; 424/714; 424/725; 424/766

(58) Field of Classification Search
None
See application file for complete search history.

(56) References Cited

U.S. PATENT DOCUMENTS

| 4,492,687 | A | 1/1985 | Herve et al. |
| 4,645,682 | A | 2/1987 | Elmore |
| 2006/0172012 | A1* | 8/2006 | Finley et al. ................... 424/523 |
| 2007/0140996 | A1* | 6/2007 | Damiani et al. ................ 424/59 |

FOREIGN PATENT DOCUMENTS

| EP | 1 304 034 A | 4/2003 |
| WO | WO 89/06904 A | 8/1989 |
| WO | WO 2004095926 | * 11/2004 |

OTHER PUBLICATIONS

International Search Report and Written Opinion from International Patent Application No. PCT/IB2008/001007, filed Jan. 25, 2008.
Youbin Si, Jing Zhou, Huaiman Chen, Dongmei Zhou: "Photostabilization of the herbicide bensulfuron-methyl by using organoclays"; Chemosphere; vol. 54; 2004; pp. 943-950; XP002490872.

* cited by examiner

*Primary Examiner* — Alton Pryor
(74) *Attorney, Agent, or Firm* — Alston & Bird LLP

(57) ABSTRACT

The invention relates to phytosanitary formulations. The phytosanitary formulations of the invention comprises at least one active ingredient and at least one alcoholic, hydro-alcoholic or aqueous extract of at least one tinctorial plant. The phytosanitary formulations of the invention can be used in the field of agriculture and horticulture, in particular.

10 Claims, 5 Drawing Sheets

PHYTOSANITARY FORMULATIONS

CROSS REFERENCE TO RELATED APPLICATIONS

This application is a national stage application filed under 35 U.S.C. 371 of International Application No. PCT/IB2008/001007, filed Jan. 25, 2008, which claims priority from U.S. Provisional Application No. 60/886,544, filed Jan. 25, 2007.

FIELD AND BACKGROUND OF THE INVENTION

The invention relates to phytosanitary formulations.

Phytosanitary formulations are widely used in agriculture and horticulture.

Phytosanitary formulations comprise an active ingredient which has an activity on the production of plants, such as compounds having fertilizer, herbicide, fungicide, pesticide or insecticide activities, and a carrier which may be liquid or solid.

Generally, phytosanitary formulations are spread under the form of a solution on the plant or on the soil in which a plant grows. But they can also be under a solid form as powders or particles which, when contacted with water, spread the active ingredient on the soil or (on) the plant.

However, phytosanitary formulations, and more precisely the active ingredient thereof, undergo degradation reactions when exposed to sunlight after spreading.

The degradation reactions not only limit the life duration of the active ingredient but also lead to the formation of by-products.

The toxicity of these by-products is very often not known but, in any case, they accumulate in the plant and can enter the alimentary chain.

To overcome and to limit the degradation of phytosanitary products, EP 0252463 proposes to entrap the active ingredient, pesticide, in polymer lattices.

A formulation comprising an active ingredient in a microcapsule and a dye which protects the active component from degradation by UV-light is proposed in WO2006/077394.

US2003/186818 teaches the use of co-products, called "soapstock", obtained in the manufacture of vegetable oils as a photo-protective agent for various applications including protection of herbicides and pesticides. The soapstock is acidulated by adding acid and the oil is recovered from the obtained acidified solution. However this oil penetrates inside the leaves leading to a loss of the photo-protective activity.

WO91/19417 teaches the use of yeast as a stabilizer for photosensitive insecticides, herbicides and insecticides and herbicide synergists. However in that case the active ingredient is no longer bio-available.

WO2005/072680 proposes to coat a horticultural active compound with a surface of doped $TiO_2$ and/or ZnO in order to increase the shelf life of horticultural formulations. However the products have some toxicity.

K. M. S. SUDARAM and J. CURRY have proposed in "Effect of some UV light absorbers on the photostabilization of azadirachtin, neem-based biopesticide" published in *Chemosphere*, Vol 32, No 4, pp 649-659, 1996, formulations containing neem-based azadirachtin insecticides and UV absorbers, to photostabilize the insecticides. However, the photo-protective agent which is used can have some toxicity because it is a synthetic product.

YASSER EL-NAHHAL and al., propose in Applied Clay Science, 14, (1999) 105-119, organo-clay based formulations for rendering less volatile and to better protect from photo-degradation commercially available emulsifiable concentrate formulations of alachlor and metolachlor. The UV absorbers are synthetic UV absorbers so that they can have some toxicity. Moreover the active ingredient is no longer bio-available.

YOUBIN SI and al., in *Chemosphere* 54 (2004) 943-950, have proposed photostable formulations of the herbicide bensulfuron-methyl. The formulations have been obtained by absorbing the herbicides on clays or on clays pre-adsorbed with the organic cation malachite green. As a consequence, the herbicides are no longer bio-available.

BLANCA CASAL and al., have proposed, in Applied Clay Science 18 (20014) 245-254, sepiolite-based materials for the photo- and thermal-stabilization of pesticides. Once again, in this case, the pesticides are no longer bio-available.

SUMMARY OF THE INVENTION

The invention aims to palliate the drawbacks of the photo-protective agents of the prior art.

For this aim, the invention proposes to add a photo-protective agent, which is a compound which is naturally produced by plants, into phytosanitary formulations to limit the degradation reactions of the active ingredient(s) of phytosanitary formulations, under UV light.

Furthermore, because the photo-protective agent used in the invention is naturally produced by plants, the source of protecting agent according to the invention is naturally renewable.

Moreover, the photo-protection of the phytosanitary formulations of the invention enables to reduce the amount of these phytosanitary formulations to be spread for a same result and to limit the formation of degradation products on the cultures.

The photo-protective agent used in the invention is an alcoholic, hydro-alcoholic or aqueous extract of a tinctorial plant. Thus, it has no toxicity.

Thus, the invention proposes a phytosanitary formulation comprising at least one active ingredient and at least one alcoholic, hydro-alcoholic, or aqueous extract of at least one tinctorial plant.

Preferably, the at least one active ingredient in the phytosanitary formulation of the invention is an herbicide.

But in another embodiment, the at least one active ingredient of the phytosanitary formulation is a pesticide.

Still another preferred embodiment of the phytosanitary formulation of the invention is a phytosanitary formulation in which the at least one active ingredient is an insecticide.

But a phytosanitary formulation according to the invention, which is also preferred, is a phytosanitary formulation in which the at least one active ingredient is a fungicide.

In all the above embodiments of the invention, preferably, the at least one tinctorial plant is chosen in the group consisting of grape, red cabbage, sorghum, common madder, yellow wood, logwood, golden tickseed, woad, annatto, beet, saffron, common turmeric, golden chamomile, black oak, elecampane, onosma, lipsticktree, henna, red sandalwood, yarrow, black cutch, green wattle, hollyhock, lady's mantle, alkanna, garden onion, European alder, desert false indigo, absinthium, common wormwood, dyer's woodruff, common buckwheat, horseflyweed, birch, yellow nicker, chestnut, giradol, European smoketree, hemp agrimony, buckwheat, queen of the meadow, glossy buckthorn, European ash, stickywilly, false baby's breath, robert geranium, elecampane inula, false yellowhead, common juniper, European privet, gypsywort, apple, high mallow, bluet, American pokeweed, forskohlii, silverweed, pomegranate, aleppo oak, English oak, Italian buckthorn, mangrove, Sicilian sumac, staghorn sumac, European black currant, lichen, bitter dock, patience dock, goat willow, basket willow, dwarf elderberry, European black elderberry, dyer's plumeless saw-wort, dyer's sorghum, Aztec marigold, French marigold, meadow-rue, tea, red clover, white clover, whortleberry, berries including blueberries, raspberries, strawberries, red maize, orange cosmos, weld, dyer's broom, common buckthorn, golden rod, indigo tree, genipa Americana, Chinese indigo, brazilwood, black cutch, myrobalan cherry plum, gambir, quebracho, chestnut, English walnut, hibiscus (bissap), carrot, red elderberry.

More preferably, the at least one tinctorial plant is chosen in the group consisting of grape, red cabbage, sorghum, common madder, yellow wood, logwood, golden tickseed, woad, annatto, beet, turmeric, hibiscus (bissap), carrot, red elderberry, orange cosmos, weld, dyer's broom, common buckthorn, golden rod, indigo tree, genipa Americana, Chinese indigo, brazilwood, black cutch, myrobalan cherry plum, gambir, quebracho, chestnut, English walnut.

But the most preferably, the at least one tinctorial plant is chosen in the group consisting of grape, red cabbage, sorghum, common madder, yellow wood, logwood, golden tickseed and woad.

In a particularly preferred embodiment of the invention, in the at least one alcoholic, hydro-alcoholic or aqueous extract, the main colouring agents are anthocyanins.

In the embodiment of the invention in which the active ingredient is an herbicide, preferably this active ingredient is sulcotrione.

BRIEF DESCRIPTION OF THE DRAWINGS

The invention will be better understood when reading the following description which will be made in connection with the figures in which.

MORE DETAILED DESCRIPTION

Figure 1:
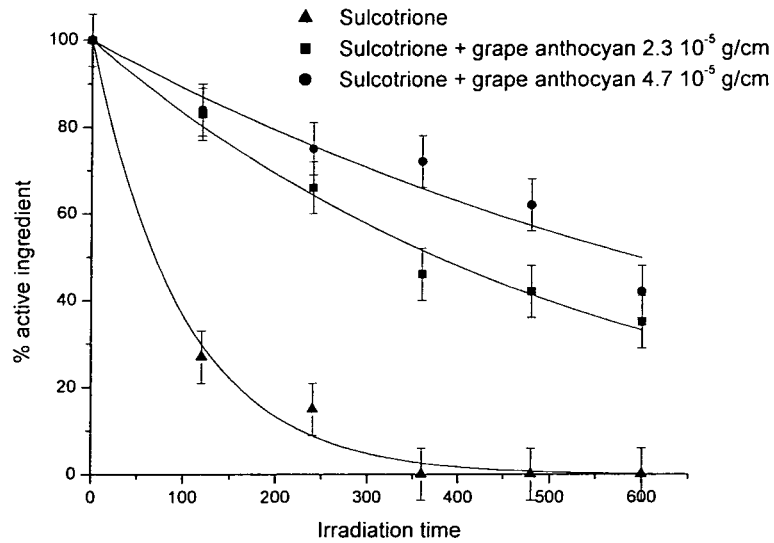
FIG. 1 shows the photo-protective effect of different concentrations of an extract of grape containing as main component anthocyanins, on the pure active ingredient, sulcotrione.

In the present description and in the appended claims, the following expressions have the following meanings:

Active ingredient: the active ingredient of the phytosanitary formulation having an activity on the plant, such as a fertilizer, herbicide, fungicide, pesticide or insecticide and a carrier which may be liquid or solid.

Tinctorial plant: a plant from which dye(s) and alimentary colouring agent(s) can be produced.

Indeed although plants such as grape, carrot, berries, beets, etc. . . . , are not generally considered as appropriate for producing dyes, they are widely used for producing colouring agents for alimentary products. They are considered as tinctorial plants in the invention because they may colour textile when smashed on this textile and that they have a photoprotective action on active ingredient of phytosanitary formulations.

As non limitative examples, some examples of tinctorial plant as defined in the invention are grape, red cabbage, sorghum, common madder, yellow wood (flustiotree), logwood, golden tickseed (coreopsis), woad, annatto, beet, turmeric, hibiscus (bissap), carrot, red elderberry, orange cosmos, weld, dyer's broom, common buckthorn, golden rod, indigo tree, genipa Americana, Chinese indigo, brazilwood, black cutch, myrobalan cherry plum, gambir, quebracho, chestnut, English walnut, plum berries including blueberries, raspberries, strawberries, red maize, saffron, common turmeric, golden chamomile, black oak, elecampane, onosma, lipsticktree, henna, red sandalwood, yarrow, black cutch, green wattle, hollyhock, lady's mantle, alkanna, garden onion, European alder, desert false indigo, absinthium, common wormwood, dyer's woodruff, common buckwheat, horseflyweed, birch, yellow nicker, chestnut, giradol, European smoketree, hemp agrimony, buckwheat, queen of the meadow, glossy buckthorn, European ash, stickywilly, false baby's breath, robert geranium, elecampane inula, false yellowhead, common juniper, European privet, gypsywort, apple, high mallow, bluet, American pokeweed, forskohlii, silverweed, pomegranate, aleppo oak, English oak, Italian buckthorn, mangrove, Sicilian sumac, staghorn sumac, European black currant, lichen, bitter dock, patience dock, goat willow, basket willow, dwarf elderberry, European black elderberry, dyer's plumeless saw-wort, dyer's sorghum, Aztec marigold, French marigold, meadow-rue, tea, red clover, white clover, whortleberry.

Agricultural alcohol: an alcohol produced from plant.

Alcoholic extract: an extract obtained by an extraction using as solvent an alcohol such as ethyleneglycol, propyleneglycol, methanol and ethanol. In the invention ethanol is preferably used.

Hydro-alcoholic extract: an extract obtained by an extraction using as solvent a mixture of an alcohol as defined above, and water.

Aqueous extract: an extract obtained by extraction using water as solvent.

Extract:

The constituents of the plants can be divided into primary metabolites and secondary metabolites.

Primary metabolites are:

glucose components such as cellulose and alginates, lipid components such as vegetable oils, amino acids and in particular lectin, structural polyphenols and in particular lignins.

The primary metabolites are produced and present in all plants.

Secondary metabolites are:

terpenoid compounds among which carotenoid compounds such as licopene, β-carotene, α-carotene, lutein, zeaxanthin and astaxatin and, non-carotenoid components such as perillyl alcohol, saponins, terpeneol, terpene, limopoidse and vitamine E components, polyphenolic compounds among which flavonoid compounds such as anthocyanins, catechins, isoflavones, hesperetin, naringin, rutin, quercetin, silymarin, tangeretin, tannins, punicalagin components, phenolic acid components such as ellagic acid, chlorogenic acid, p-coumaric acid, phytic acid, ferulic acid, vanillin, cinnamic acid, hydroxycinnamic acids and gallic acid, and other non-flavonoid components such as curcumin, resveratrol, lignans, glucosinolate components among which isothiocyanates such as phenethyl, isothiocyanate, benzyl, sulphoraphane components, and indoles components such as indole-3-carbinol, thiosulfonates components, phytosterol components such as β-phytosterols, anthraquinone components such as senna, barbaloin and hypericin components, capsaicin components, piperine components, chlorophyll, betaine, pectin, oxalic acid.

It is to be noted that the secondary metabolites produced and present in a plant depend on the plant itself, which means that a plant may produce only some of these secondary metabolites.

When extracting a plant with alcohol, water or a mixture of water and alcohol, the obtained extract does not contain the glucose components, the lipid components, and the structural polyphenols components.

Otherwise stated, the extract used in the invention contains the amino acid components and some or all the secondary metabolite components.

Main component: component which is in the greater concentration.

Is mainly: is the component in the greater concentration.

The surface of leaves of plants is covered with a thin lipidic film which constitutes a barrier limiting the penetration of the xenobiotic products. This barrier also reduces the water losses of the plant. After spreading, the phytosanitary products remain a certain time in this cuticular zone. As long as they are in this cucitular zone, the phytosanitary products are submitted to the degradating effect of the sun radiations.

To limit the photodegradation enables to lengthen the life duration of the phytosanitary products with two consequences: to lengthen its duration of action and to reduce the production of by-products, the toxicity of which is often not determined.

Furthermore, it is now recognized that only a small part of the active ingredients spread on the plant reaches its target. To reduce the losses by photochemical transformation enables to lower the amount of active ingredients spread during the treatment.

In the case of treatment by herbicides, one aims at eliminating weeds but the cultivated plants receive the same dose as weeds. The active ingredient or its by-products accumulate in the plant and it is preferable to prevent the uncontrolled formation of by-products with unknown effects.

In the case of treatment with insecticides, the cultivated plant itself is treated. The persistence of the insecticide at the surface of the plant is essential.

It is recognized that the active ingredient is accumulated in the cuticular wax before penetrating in the leaves. In fact, it is the main location of photochemical reactions.

Consequently, to demonstrate the effect of adding extract of plant in commercial formulations of phytosanitary products, the inventors have conducted photochemical studies, firstly on thin films of cuticular wax which are recognized as a model system of the surface of the leaves, and, secondly on maize plants planted in a field.

The methodology for conducting the tests on thin films of cuticular wax comprises the following steps:

Preparation of the wax film: the wax which is used is the commercial carnauba wax.

Adding the pesticide. On the one hand, the active ingredient, sulcotrione, and on the other hand, the commercial formulation, Mikado®(alone or with the adding of at least one extract of at least one tinctorial plant, is deposited under the form of an aqueous solution on the surface of the leaves. The amount of active ingredient deposited by surface unit is equivalent to the amount used in agriculture. The studies are conducted after evaporation of the water.

Recovering of the pesticide. The films are rinsed with water and analysed by HPLC. It has been checked that the step of recovering is quantitative.

Tests in darkness. The concentration of the active ingredients on the surface of the leaves in darkness is controlled in order to measure the penetration rate of the active ingredient in the films and its volatilisation. It has been showed that very little active ingredients volatilize under these test conditions and that the active ingredient penetrates slowly into the films.

Irradiation. Irradiation tests are conducted in a Suntest reactor simulating solar rays in temperate countries.

The photoprotective effects of the extracts according to the invention have been evaluated as follows The surface concentration of the active ingredient (sulcotrione) on the wax films is of $0.76 \cdot 10^{-5}$ g/cm$^2$, the active ingredient being used either pure or under the form of a commercial formulation. These concentrations are representative of the conditions of use in agriculture (100 to 300 g of active ingredient by hectare). The surface concentration of the natural pigments is comprised between $4.7 \cdot 10^{-5}$ g/cm$^2$ and $1 \cdot 10^{-4}$ g/cm$^2$, i.e. about 1.5 to 6 times the amount of active ingredient.

The wax films pulverised with the phytosanitary formulation alone or according to the invention containing both the active ingredient (here, sulcotrione) and the extract of plant as defined in the invention at the desired concentration, are then irradiated in the Suntest reactor previously described.

The results of this test are given in the following examples which are only illustrative and not limitative of the scope of the invention.

Example 1

Photo-Protective Effect of Grape Extract

The grape extract used in this example is an ethanolic extract.

It contains, as main colouring agents, anthocyanins.

Some anthocyanins in this grape extract are in particular delphinidin, cyanidin, petunidin, peonidin, and malvidin. These particular anthocyanins may be present as aglycone, or glucosyl, or coumaryl derivatives.

In a first step, the protective effect of the active ingredient, sulcotrione, alone has been studied.

FIG. 1 shows the weight percentage of active ingredient remaining in the wax film as a function of the irradiation duration for the active ingredient alone, for the active ingredient to which an amount giving a surface concentration of 2.3 10$^{-5}$ g/cm$^2$ of grape extract has been added and for the active ingredient to which an amount giving a surface concentration of 4.7 10$^{-5}$ g/cm$^2$ of grape extract has been added.

As it can be seen from FIG. 1, the half-life of the pure active ingredient is 1 h 10 min. When an amount giving a surface concentration of 2.3 10$^{-5}$ g/cm$^2$ of grape extract is added to the active ingredient, the half-life of the mixture is of 6 h15 min. When an amount of grape extract giving a surface concentration of 4.7 10$^{-5}$ g/cm$^2$ is added to the active ingredient, then the half-life is of 10 hours.

Thus, the half-life of the active ingredient is multiplied by 5.3 to 8.5 according to the amount of added grape extract.

In a second step, a commercial formulation, Mikado®, containing the same active ingredient, sulcotrione, has been studied in the same conditions.

Figure 2:
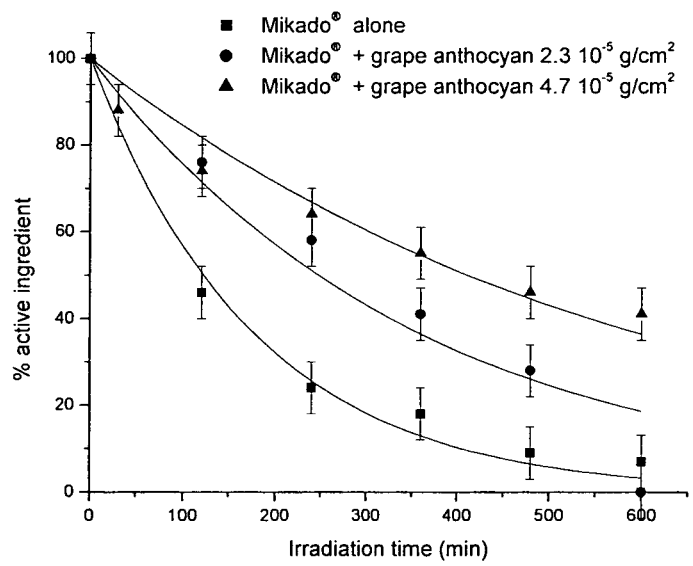
FIG. 2 shows the photo-protective effect of different concentrations of an alcoholic extract of grape, containing as main component anthocyanins, on a formulated pesticide, known as Mikado®, i.e. a commercial formulation containing sulcotrione.

FIG. 2 shows the weight percentage of active ingredient remaining in the wax film, as a function of the irradiation duration of the film when using the commercial formulation alone, the commercial formulation to which an amount giving a surface concentration of 2.3 10$^{-5}$ g/cm$^2$ of grape extract has been added and the commercial formulation to which an amount giving a surface concentration of 4.7 10$^{-5}$ g/cm$^2$ of grape extract has been added.

As it can be seen from FIG. 2, with the addition of grape extract, a clear slowing down of the transformation rate is observed. Thus, the half-life of the active formulation, which is of about 2 hours without photoprotective agent, is of 7 hours when an amount giving a surface concentration of 4.7 10$^{-5}$ g/cm$^2$ of grape extract is added to the commercial formulation and of about 4 hours when an amount giving a surface concentration of 2.3 10$^{-5}$ g/cm$^2$ of grape extract is added to the commercial formulation.

Thus, the half-life of the active ingredient is also multiplied by 2 when grape extract is added to the commercial formulation.

To summarize, grape extract enables to multiply by 2 to 3.5 the half-life of the pesticide, according to the amount of added plant extract.

The same tests have been conducted with red cabbage anthocyan and with sorghum anthocyan.

Example 2

Photo-Protective Effect of Red Cabbage Extract

The extract of red cabbage used in this example is an ethanolic extract.

The red cabbage extract used in the invention mainly contains, as colouring agents, anthocyanins, and more particularly acylated anthocyanins.

Figure 3:
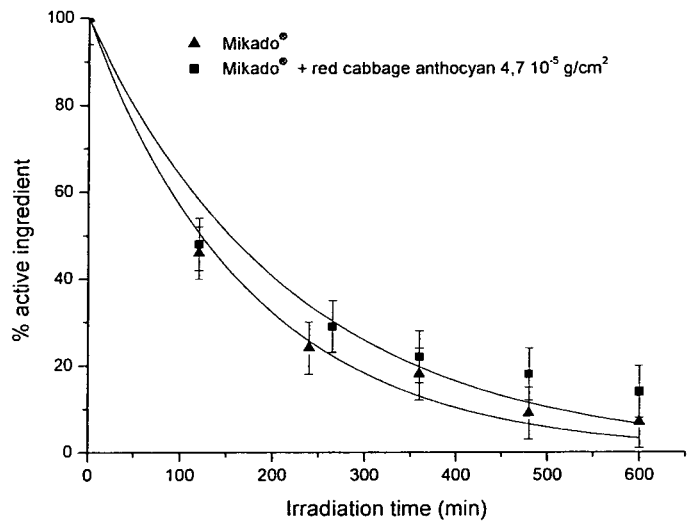
FIG. 3 shows the photo-protective effect of different concentrations of an extract of red cabbage containing mainly anthocyanins on the pure ingredient, sulcotrione.

FIG. 3 shows the photoprotective effect of red cabbage extract.

Indeed, as it can be seen from FIG. 3, a slow-down of the transformation rate of the active ingredient is observed when comparing the percentage of active ingredient on the surface of the wax film as a function of the irradiation time when using the commercial formulation alone or when using this commercial formulation to which an amount giving a surface concentration of 4.7 10$^{-5}$ g/cm$^2$ of red cabbage extract has been added.

Example 3

Photo-Protective Effect of Sorghum Extract

A commercial sorghum extract has been used in this example. This commercial extract is sold under the tradename "Sorgho Extrait vegetal colorant brun C10" (batch 021415) by the Company Couleur de Plante.

This sorghum extract contains as main colouring components anthocyanins and in particular apigeninidin and luteolinidin derivatives.

Figure 4:
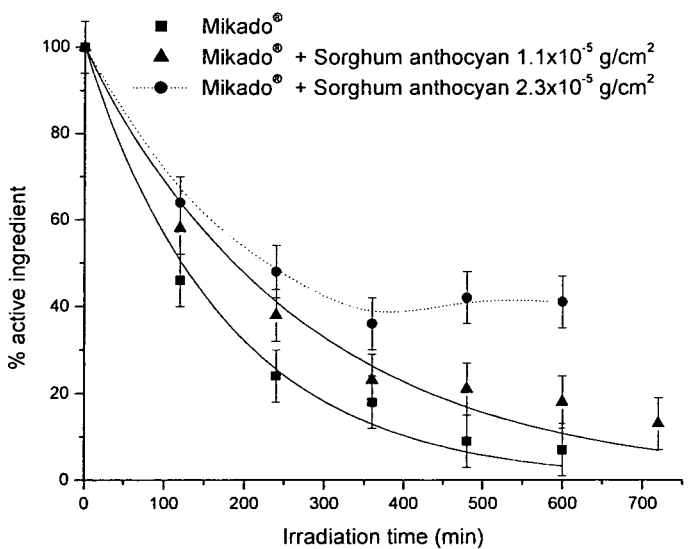
FIG. 4 shows the photo-protective effect of different concentrations of an extract of sorghum, containing mainly anthocyanins, on the formulated pesticide Mikado®.

FIG. 4 shows the photo-protective effect of sorghum extract. As it can be seen from FIG. 4, the half-life of the active ingredient is 3 h when sorghum extract in an amount giving a surface concentration of 1.1 10$^{-5}$ g/cm$^2$ of sorghum extract is added, which is more than two times the half life of the commercial formulation without sorghum extract.

When an amount giving a surface concentration of 2.3 10$^{-5}$ g/cm$^2$ of sorghum extract is added to the commercial formulation, after 6 hours of irradiation, 40% of the active ingredient is still remaining.

Examples 1 to 3 above show that the plant extract to be used in the invention is preferably a plant extract comprising anthocyanins as main colouring components.

But the use of an extract of plant presents great advantages over the use of only its main components which in the case of anthocyanins are also the colouring components of the extract.

Firstly, using a plant extract avoids using complex procedures for purifying the colouring compound of the plant extract and also avoids introducing residual products used during this purification in particular in the alimentary chain. It is also less time consuming. But the most important advantage of using all the plant extract itself is that the presence of the other components of the extract and, in particular of polyphenolic compounds increases coloration, stabilizes the colour of the plant extract and also enables to obtain a better solubility of the plant in water.

Indeed, although the photo-protective effect of the plant extract of the invention could be attributed to the colouring agent which is the UV-absorber of the extract it contains, it has now been discovered that using the pure colouring agent alone has less photo-protective effect than its mixture with the other components of the extract of plant used in the invention.

Indeed, when comparing the UV-absorbance of pure rutin, a flavonoid component of a plant extract, which is also one of the colouring agent of the plant extract, and therefore which is the UV-absorber of the plant, and the UV-absorbance of pure gallic acid, which is a phenolic acid component of the plant, which is not coloured, with the UV-absorbance of a mixture of rutin and gallic acid, one sees that the UV absorbance of the mixture is higher than the UV-absorbance of the rutin plus the UV-absorbance of gallic acid in the area of UV-wavelengths. Therefore the photo-protective effect of the mixture is higher than the photo-protective effect of rutin plus the photo-protective effect of gallic acid.

Figure 9:
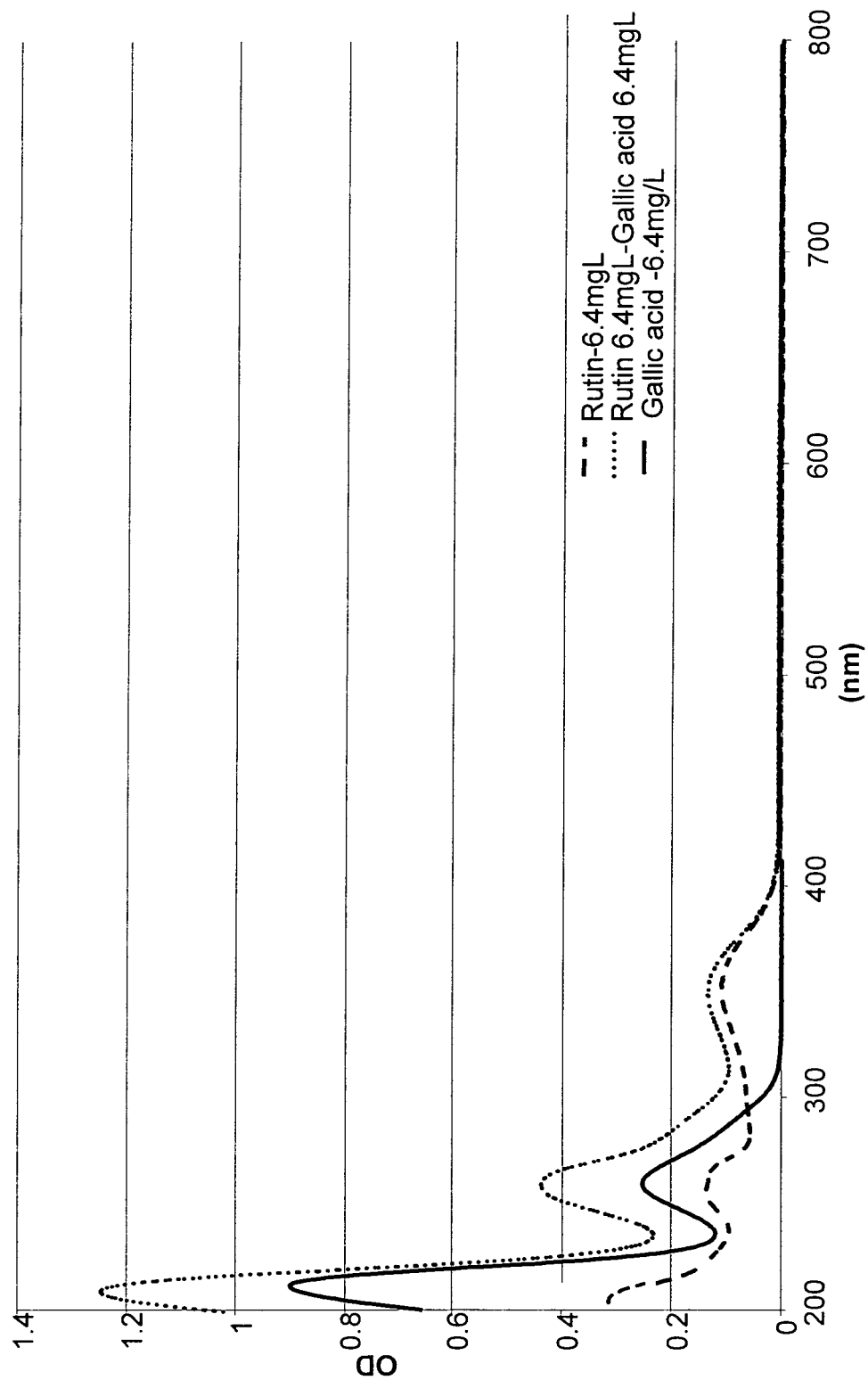
FIG. 9 shows the UV-absorbance spectrum of pure rutin, of pure gallic acid and of a mixture of rutin and gallic acid.

FIG. 9 shows the absorbance spectrum of pure rutin, of pure gallic acid, and of a 50/50 mixture of rutin and gallic acid.

One can see from FIG. 9, that in the wavelength of UV, i.e. from 300 to 400 nm, the absorbance of the mixture is higher than the absorbance of pure rutin plus the absorbance of pure gallic acid Example 4

Photo-Protective Effect of Yellow Wood Extract

The extract of yellow wood (*Morus Tincotoria*) used in this example is a commercial extract sold under the tradename "Extrait de bois jaune (*Morus Tincotoria*)" by the Company SCRD.

Figure 5:
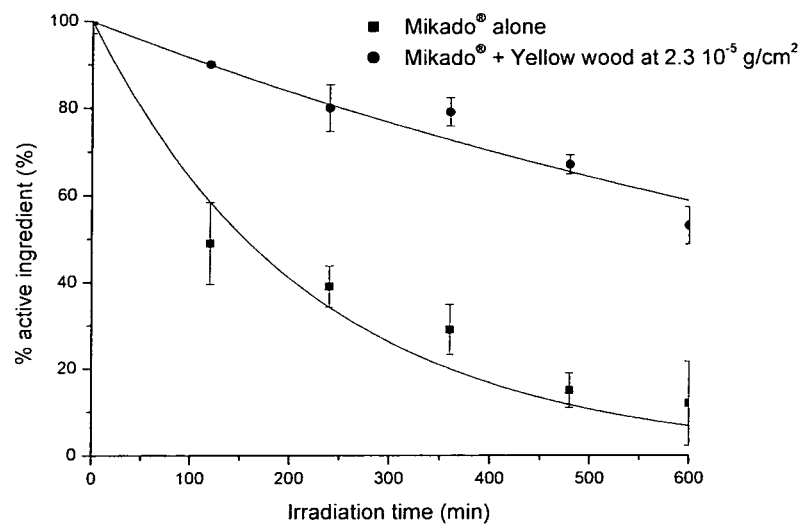
FIG. 5 shows the photo-protective effect of different concentrations of an extract of yellow wood on the formulated pesticide Mikado®.

FIG. 5 shows the photo-protective effect of yellow wood extract.

As it can be seen from FIG. 5, the half-life of the commercial formulation Mikado® alone is of 2 h30 whereas the half-life of the commercial formulation Mikado® in which an amount giving a surface concentration of 2.3 $10^{-5}$ g/cm² of yellow wood extract is added is higher than 10 hours.

Example 5

Photo-Protective Effect of Logwood Extract

The logwood extract used in this example is a commercial logwood extract sold under the tradename "Extrait de Campêche (*Heamatoxylum campachianum*)" sold by the Company SCRD.

Figure 6:
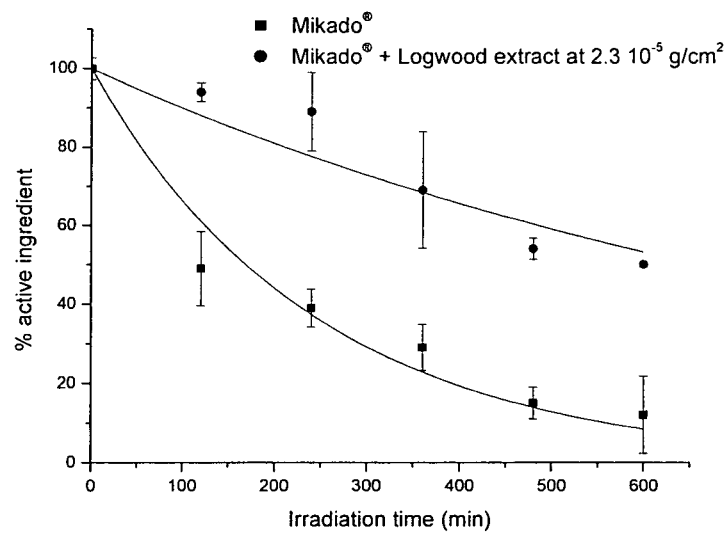
FIG. 6 shows the photo-protective effect of different concentrations of an extract of logwood on the commercial formulation Mikado®.

FIG. 6 shows the photo-protective effect of the logwood extract on the commercial formulation Mikado®.

As it can be seen from FIG. 6, the half-life of the commercial formulation Mikado® is of 2 h30 when no logwood extract is added, whereas the half-life of this commercial formulation Mikado® is higher than 10 hours when the logwood extract is added in the Mikado® formulation at an amount giving a surface concentration of 2.3 $10^{-5}$ g/cm² of logwood extract.

Example 6

Photo-Protective Effect of Coreopsis (Golden Tickseed) Extract

The Coreopsis extract used in this example is a commercial Coreopsis extract sold under the tradename "Coréopsis Extrait végétal colorant orange CO1" (Batch 05-31) by the Company Couleur de Plante.

Figure 7:
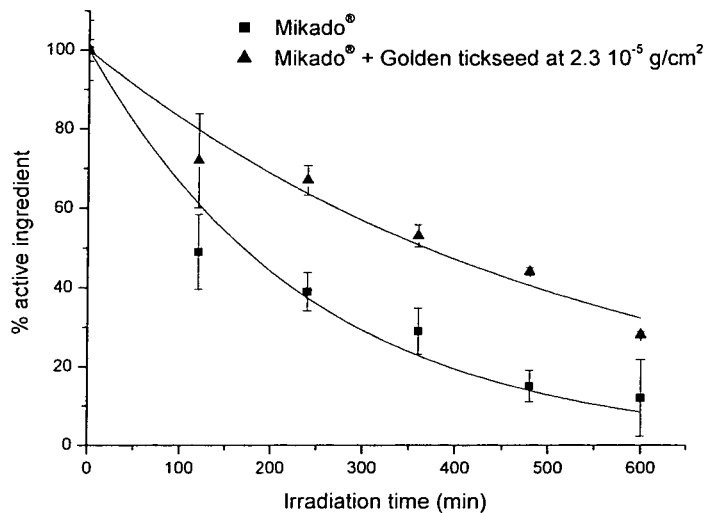
FIG. 7 shows the photo-protective effect of different concentrations of an extract of golden tickseed on the commercial formulation Mikado®.

FIG. 7 shows the photo-protective effect of Coreopsis on the active ingredient (sulcotrione) used under the form of the commercial formulation Mikado®

As it can be seen from FIG. 7, the half-life of sulcotrione is of 2 h30 when alone whereas the half-life of sulcotrione is of 6 h20 when an amount giving a surface concentration of 2.3 $10^{-5}$ g/cm² of Coreopsis extract extract is added to Mikado®.

Example 7

Photo-Protective Effect of Woad Extract

The woad extract used in this example is a commercial woad extract sold under the tradename "Bleu de Pastel" by the Company CAPA.

Figure 8:
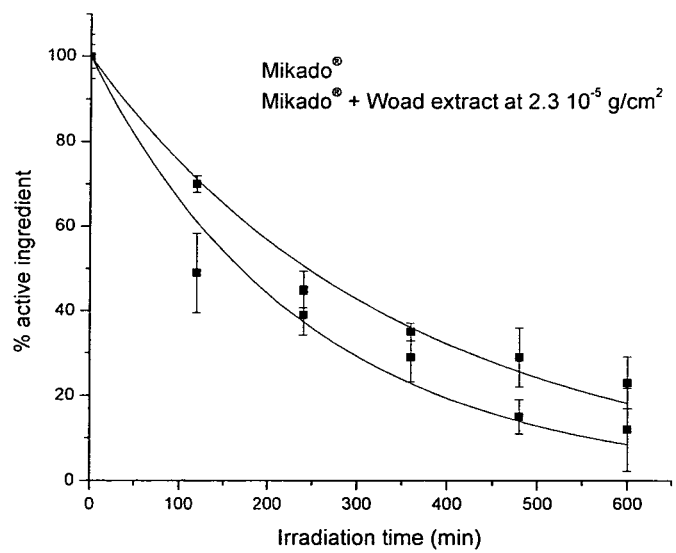
FIG. 8 shows the photo-protective effect of different concentrations of an extract of woad on the commercial formulation Mikado®.

FIG. 8 shows the photo-protective effect of the woad extract on the active ingredient, sulcotrione, on the commercial phytosanitary formulation Mikado®.

As it can be seen from FIG. 8, the half-life of sulcotrione in the formulation of Mikado® alone is of 2 h30, whereas the half-life of sulcotrione in the formulation of Mikado® to which an amount giving a surface concentration of 2.3 $10^{-5}$ g/cm² of woad extract is added is of 4 h 10.

The effect of adding the plant extract(s) according to the invention to the active ingredient, sulcotrione, alone or to a commercial phytosanitary formulation, Mikado®, comprising this active ingredient sulcotrione, on the stability of the active ingredient after 6 and 10 hours of UV-irradiation is summarized in the following Table 1.

Durations of UV exposure of 6 and 10 hours have been chosen because sulcotrione is a herbicide so that it needs from a couple of hours to more than ten hours to enter the leaves to have it "killing" effect on weeds.

Therefore, it is important that the herbicide maintains a maximum of its activity at least ten hours under UV-exposure.

TABLE 1

Weight percentage of active ingredient remaining after six and ten hours of UV irradiation

| Tested Composition | Weight percentage of remaining active ingredient after 6 hours of UV exposure | Weight percentage of remaining active ingredient after 10 hours of UV exposure |
|---|---|---|
| Active ingredient + 3 times the amount of active ingredient of grape extract | 46% | 35% |
| Active ingredient + 6 times the amount of active ingredient of grape extract | 72% | 42% |
| Commercial formulation alone | 18% | 7% |
| Commercial formulation + 1.5 times the amount of active ingredient of sorghum extract | 23% | 13% |
| Commercial formulation + 3 times the amount of active ingredient of red cabbage extract | 22% | 14% |
| Commercial formulation + 3 times the amount of active ingredient of common madder extract | 25% | 18% |
| Commercial formulation + 3 times the amount of active ingredient of grape extract | 41% | 20% |
| Commercial formulation + 3 times the amount of active ingredient of sorghum extract | 36% | 40% |
| Commercial formulation + 3 times the amount of active ingredient of Yellow wood extract | 79% | 53% |

TABLE 1-continued

Weight percentage of active ingredient remaining after six and ten hours of UV irradiation

| Tested Composition | Weight percentage of remaining active ingredient after 6 hours of UV exposure | Weight percentage of remaining active ingredient after 10 hours of UV exposure |
|---|---|---|
| Commercial formulation + 3 times the amount of active ingredient of logwood extract | 69% | 50% |
| Commercial formulation + 3 times the amount of active ingredient of a golden tickseed extract | 53% | 28% |
| Commercial formulation + 3 times the amount of active ingredient of a woad extract | 35% | 23% |
| Commercial formulation + 6 times the amount of active ingredient of grape extract | 55% | 40% |

After six hours of irradiation, only 5-10% of the pure active ingredient remain on the leaves, when pure sulcotrione is used. To add a plant extract according to the invention enables to maintain up to 72% of the active ingredient after six hours of irradiation, as it can be seen from Table 1.

When the commercial formulation Mikado® is used without adding an extract of plant according to the invention, after six hours of irradiation, 18% of active ingredient remain on the leaves. But, when a plant extract according to the invention is added to this commercial formulation, up to 79% of the active ingredients remain.

After ten hours of irradiation, only 7% of the active ingredient remain when the commercial formulation is used alone.

Still after ten hours of irradiation, to add yellow wood extract is the more effective. Indeed, up to 53% of the active ingredient remain after ten hours of irradiation when yellow wood extract is added to the commercial formulation in an amount three times higher than the one of the active ingredient.

To conclude, after a day of exposure to the sun, the adding of plant extract enables to really protect the active ingredient against degradation.

Therefore, by adding photoprotective plant extract, one can improve the efficacy i.e. the duration of action of a phytosanitary product.

In the case of herbicides, during the night following the treatment, the active ingredient which has not been degraded during the preceding day can continue to penetrate into the leaves for reaching its biological target. This is important because it is recognized that the penetration of the active ingredient in the leaves is very often a factor limiting the efficacy of an herbicide.

The phytosanitary formulation of the invention thus enables to increase the time during which the active ingredient (herbicide) can enter in the leaves and consequently increases its efficacy.

Adding a plant extract also enables to limit the amount of product spread on the cultures. In the case of fungicides or insecticides, the active ingredient on the surface of the leaves or fruits (which is its action site) is protected from the sunlight and therefore its action is lengthened.

In the practice, the active formulations are spread in presence of formulation agents which facilitate the dispersion on the surface of the leaves and the penetration in the plant (in the case of herbicides). The question of the behaviour of the active ingredient under sunlight is not very well documented.

In fact, when requesting homologation of phytosanitary products, only tests of photodegradation in water and on the soils are required but tests on vegetal surfaces are not required. However, it is widely admitted in the literature that phototransformation on the plants is a major factor of dissipation of the active ingredient after spreading.

The result of these tests with sulcotrione, which is a molecule having an half-life of about 80 days in water, shows that this half-life can be of only 1 h30 min on the surface of the leaves.

The validity of these results has been confirmed by tests conducted on maize plants planted in a field.

For this aim, the commercial formulation, Mikado®, has been spread on maize plants planted in a field.

The amount of sulcotrione and the formation of a by-product of the phototransformation on the surface of the leaves have been checked by HPLC.

The obtained chromatograms showed that after one hour, 25% of sulcotrione is transformed.

Thus the half-life of sulcotrione measured in the laboratory of the inventors is similar to the one found when sulcotrione is spread on maize plants planted in a field.

After 24 hours, sulcotrione is no longer detected on the surface of the leaves of the maize plants whereas the product of phototransformation is still detected. This product accumulates in the leaves.

Although the tests reported above have been conducted using sulcotrione as a pesticide and maize as a model plant, it will clearly appear to the man skilled in the art that the adding of plant extract for protecting any type of phytosanitary products such as insecticides, fungicides and herbicides and for the treatment of any type of cultures (vegetables, fruits) will product the same photoprotective effect as demonstrated above.

Furthermore, the adding of this plant extract in phytosanitary formulations has a supplementary advantage: the pigment renders the product visible after its spreading or its pulverization thus enabling to have one uniform spreading without loss of product.

The process of manufacturing the phytosanitary formulations of the invention comprises the addition of the appropriate amounts of plant extract to the active ingredient, directly, or into the formulated active ingredient.

Although in all the above examples, only one extract of one type of tinctorial plant has been added in the phytosanitary formulation, it will clearly appear to the man skilled in the art that mixtures of extracts of different tinctorial plants, as defined in the invention, will provide the same beneficial effects.

The invention claimed is:

1. Method for photo-protecting or photo-stabilizing an active ingredient of a phytosanitary formulation applied to a plant, said method comprising the following steps:
   a) adding at least one alcoholic, hydroalcoholic or aqueous extract of at least one tinctorial plant to said phytosanitary formulation,
   b) applying the mixture obtained at step a) to the plant,
   wherein the extract of the at least one tinctorial plant contains anthocyanin and the active ingredient is a pesticide, and wherein the at least one alcoholic, hydroalcoholic or aqueous extract of the at least one tinctorial plant increases the half-life of the pesticide.

2. Method according to claim 1 wherein said pesticide is an herbicide.

3. Method according to claim 1 wherein said pesticide is an insecticide.

4. Method according to claim 1 wherein said pesticide is a fungicide.

5. Method according to claim 1 wherein the at least one tinctorial plant is chosen from the group consisting of grape, red cabbage, sorghum, common madder, yellow wood, logwood, golden tickseed, woad, annatto, beet, saffron, common turmeric, golden chamomile, black oak, elecampane, onosma, lipsticktree, henna, red sandalwood, yarrow, black cutch, green wattle, hollyhock, lady's mantle, alkanna, garden onion, European alder, desert false indigo, absinthium, common wormwood, dyer's woodruff, common buckwheat, horseflyweed, birch, yellow nicker, chestnut, giradol, European smoketree, hemp agrimony, buckwheat, queen of the meadow, glossy buckthorn, European ash, stickywilly, false baby's breath, robert geranium, elecampane inula, false yellowhead, common juniper, European privet, gypsywort, apple, high mallow, bluet, American pokeweed, forskohlii, silverweed, pomegranate, aleppo oak, English oak, Italian buckthorn, mangrove, Sicilian sumac, staghorn sumac, European black currant, lichen, bitter dock, patience dock, goat willow, basket willow, dwarf elderberry, European black elderberry, dyer's plumeless saw-wort, dyer's sorghum, Aztec marigold, French marigold, meadow-rue, tea, red clover, white clover, whortleberry, berries including blueberries, raspberries, strawberries, red maize, orange cosmos, weld, dyer's broom, common buckthorn, golden rod, indigo tree, genipa Americana, Chinese indigo, brazilwood, black cutch, myrobalan cherry plum, gambir, quebracho, chestnut, English walnut, hibiscus (bissap), carrot and red elderberry.

6. Method according to claim 1 wherein the at least one tinctorial plant is chosen from the group consisting of grape, red cabbage, sorghum, common madder, yellow wood, logwood, golden tickseed, woad, annatto, beet, turmeric, hibiscus (bissap), carrot, red elderberry, orange cosmos, weld, dyer's broom, common buckthorn, golden rod, indigo tree, genipa Americana, Chinese indigo, brazilwood, black cutch, myrobalan cherry plum, gambir, quebracho, chestnut and English walnut.

7. Method according to claim 1 wherein the at least one tinctorial plant is chosen from the group consisting of grape, red cabbage, sorghum, common madder, yellow wood, logwood, golden tickseed and woad.

8. Method according to claim 1 wherein the active ingredient is sulcotrione.

9. Method according to claim 1,
   wherein the application is a foliar application.

10. Method according to claim 1, wherein the extract is an ethanolic extract.

* * * * *